United States Patent [19]
Sato et al.

[11] Patent Number: 5,964,725
[45] Date of Patent: Oct. 12, 1999

[54] GAS EXCHANGE APPARATUS USING IMPROVED SILICONE RUBBER HOLLOW FIBER

[75] Inventors: Koshiro Sato, Tokyo; Masanori Katayama, Hayama-machi, both of Japan

[73] Assignee: Fuji Systems Corporation, Tokyo, Japan

[21] Appl. No.: 08/841,520

[22] Filed: Apr. 23, 1997

[30] Foreign Application Priority Data

Apr. 24, 1996 [JP] Japan ................................ 8-102660

[51] Int. Cl.⁶ .................................................. A61M 37/00
[52] U.S. Cl. ................................................. 604/4; 422/48
[58] Field of Search ................ 422/45–48; 128/205.28, 128/DIG. 3; 210/321.8

[56] References Cited

U.S. PATENT DOCUMENTS

| | | | |
|---|---|---|---|
| 4,770,852 | 9/1988 | Takahara et al. | 422/48 |
| 4,808,378 | 2/1989 | Nakanisha et al. | 422/48 |
| 5,106,579 | 4/1992 | Fukazawa et al. | 422/48 |
| 5,139,741 | 8/1992 | Hagiwara | 422/48 |
| 5,162,102 | 11/1992 | Nogawa et al. | 422/48 |

*Primary Examiner*—John G. Weiss
*Assistant Examiner*—Ki Yong O
*Attorney, Agent, or Firm*—Gifford, Krass, Groh, Sprinkle, Anderson & Citkowski, P.C.

[57] ABSTRACT

A gas exchange apparatus for use as a artificial lung incorporates a hollow fiber module for bundling a plurality of thin-walled hollow silicone fibers. The fibers are wound in the form of a twilled pattern so as to form an internal perfusion passage and an external perfusion passage. A housing encloses the hollow fiber module. The housing incorporates a first inlet and outlet formed on the housing for communication of gas or liquid with the internal perfusion passage, and a second inlet and outlet formed for communication of gas or liquid with the external perfusion passage.

2 Claims, 5 Drawing Sheets

GAS EXCHANGE APPARATUS USING IMPROVED SILICONE RUBBER HOLLOW FIBER

BACKGROUND OF THE INVENTION

1. Field of the Invention

The present invention relates to a gas exchange apparatus employing the silicone rubber hollow fiber composed of a silicone rubber composition for use as an artificial lung by being connected to the external blood circulation circuit, an artificial "gill" as a liquid-to-gas phase gas exchanger, and further an oxygenator and disoxidizer for liquid and gas.

2. Brief Description of the Prior Art

As a conventional gas exchanger, there has been known a membrane-type artificial lung disclosed in Japanese Patent Publication No. 3-60508 (1991), in which gas exchange operation is performed through a porous gas exchange membrane having a plurality of minute or fine openings formed therethrough and serving as gas flow passages, wherein a kind of fine particles are maintained in the fine openings to reduce the sectional area, and, in addition, an anti-coagulant for blood is retained in the fine particles themselves or between these particles. Such a retention function of the agent contributes to prevent leakage of components of blood, such as water or, during a long-term circulation, and also to prevent production of thrombus on the surface of gas exchange membrane, thereby the out-body circulation being enabled with a small amount of heparin supplement.

However, the gas exchange rate was not satisfactory in either of the conventional gas exchanger, since fine particles are confined in fine openings using "porous hollow fiber" for preventing sealum leakage in the first example, and "silicone membrane hollow fiber" having an increased wall thickness is used in the second embodiment. Therefore, there have been problems, when the exchange rate is increased, the dimension of the apparatus, that is, of the artificial lung increases, resulting in an increased quantity of blood, namely the priming volume, which is filled in the apparatus. In contrast, the reduced priming volume, although providing a small size, the quantity of gas exchange is accordingly decreased, and, therefore, the gas exchange rate is lowered.

As a conventional silicone rubber hollow fiber in use for gas exchangers, using a silicone rubber composition, there was a Japanese patent application No.61027/1996 proposed by the same applicant.

The hollow fiber of the invention is formed of a silicone rubber composition of a blend of silicone rubber compound and liquid silicone rubber or silicone oil, and may be produced by setting the ratio of sectional area $S_1:S_2$ in the range of 1:0.5 to 1:0.01 when the silicone rubber composition is extruded in a form of tube and oriented under heating in a vulcanizer, wherein $S_1$ is a sectional area of a tube extruded from a nip between a die and a nipple of an extruder and $S_2$ is a sectional area of a tube oriented.

The outer diameter of the hollow fiber obtained is less than 300 microns and wall thickness thereof is less than 50 microns. SS are values obtained by the following equations.

$$S_1 = \pi(r_1/2)^2 - \pi(r_2/2)^2$$

$$S_2 = \pi(r_3/2)^2 - \pi(r_4/2)^2$$

Where, $r_1$: an inner diameter of the die;
$r_2$: an outer diameter of nipple;
$r_3$: an outer diameter of hollow thread; and
$r_4$: an inner diameter of hollow thread.

The silicone rubber composition aforementioned is formed by adding a silica as a filler to a silicone rubber compound of dimethylsiloxane and/or dimethylvinylsiloxane as a silicone rubber compound and making use of addition curing-type silicone rubber compound having a hardness of more than 75 (JIS-A) measured by JISK-6301 and a tear strength of more than 40 Kg/cm (Type-A), an organopolysiloxane having a viscosity in the range of 100 tO 100,000 poise at 25° C. containing a vinyl group as an aforesaid silicone rubber and an silicone oil having the same viscosity as that of the organopolysiloxane as above-mentioned silicone oil.

Since the conventional silicone rubber composition is, as described above, formed by mixing a silicone rubber compound with a liquid silicone rubber or silicone oil, a silica agglomerated in the silicone rubber may be dispersed uniformly. Therefore, the conventional silicone rubber becomes a state which cannot be easily cut even the silicone rubber composition is extruded in the form of tube. And also, since the conventional silicone rubber composition is, as described, formed by mixing a silicone rubber compound with a liquid silicone rubber or silicone oil, the chain of high polymer interlocking in the silicone rubber is unravelled, the orientation property of the silicone rubber can be remarkably improved. For the reasons as above, the conventional silicone rubber composition is available to produce a fine and thin-gage silicone rubber hollow fiber having an outer diameter of less than 300 microns and a wall thickness of less than 50 microns.

While the hollow fiber itself could be produced by the conventional silicone rubber composition since the orientation treatment is carried out under a decrease of plasticity by mixing an uncured silicone rubber composition, there is a case where the hollow fiber has the tensile loading ($M_{100}$) (100% modulus of which is not sufficient, that is less than 5 grams is produced when the wall thickness is less than 40 microns. Therefore, there occur the troubles such as an elongation set or cut-through of the hollow fiber at a fabrication step, which gives rise to a problem that only a hollow fiber having a wall thickness of approximate 50 microns can be stably produced.

SUMMARY OF THE INVENTION

The U.S. patent application Ser. No. 08/720,052 filed on Sep. 27, 1996, in which a gas exchange apparatus by the same applicant is disclosed, is incorporated herein by reference.

As shown in FIG. 1, a gas exchange apparatus for use as an artificial lung according to the invention is fundamentally comprised of a hollow fiber module $M_1$ formed by bundling a plurality of silicone thin-walled hollow fibers wound in the form of a twilled pattern so as to form an internal perfusion passage and an external perfusion passage; a housing $H_1$ for enclosing the hollow fiber module; a first inlet A and a first outlet B formed on the housing $H_1$ for gas or liquid for communication with the internal perfusion passage; and a second inlet C and a second outlet D formed on the housing for gas or liquid for communication with the external perfusion passage.

The object of the present invention is to solve the problems of the prior art apparatus, and further to provide a silicone rubber hollow fiber used in a gas exchanger having a tensile load ($M_{100}$) of more than 5 grams and an outer diameter of less than 400 microns as well as a wall thickness of less than 50 microns.

DETAILED DESCRIPTION OF THE PREFERRED EMBODIMENTS

Figure 1A:
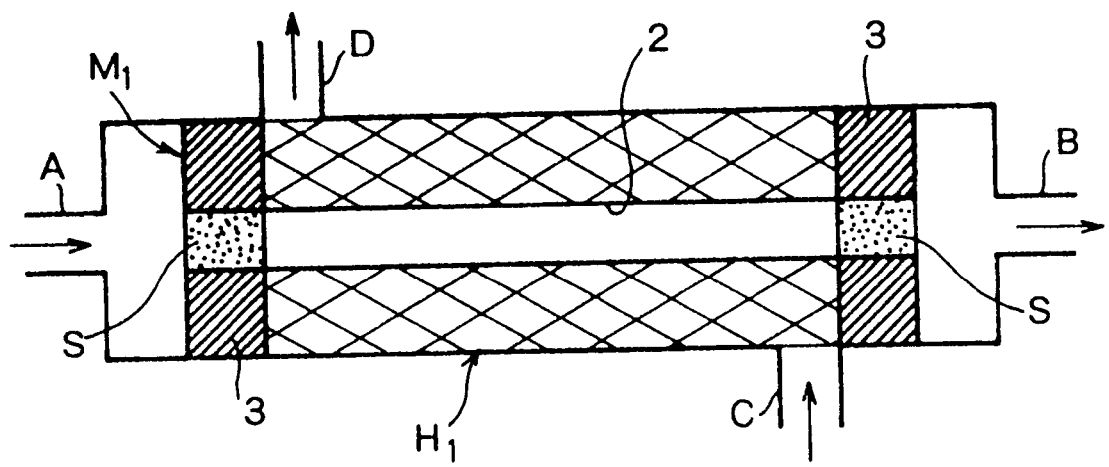
FIGS. 1a and 1b are sectional views schematically illustrating a gas exchange apparatus according to an embodiment of the invention.
Figure 1B:
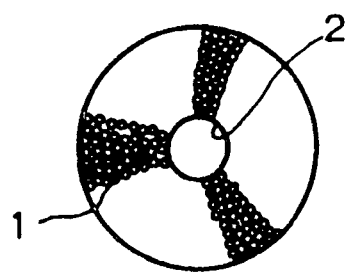

A hollow fiber module $M_1$ is fabricated in that, as shown in FIG. 1, the silicone rubber hollow fiber 1 is wound around a core 2 in the form of twill figure with the angle of 30 to 160° with the hollow fibers at both ends being sealed with silicone resin to each other, and thereafter the sealed portions are cut in the radial direction to allow the ends of hollow fiber 1 to be freed. Therefore, the module $M_1$ is in the form that hollow fibers 1 each having a prescribed length are bundled in the twill form around the core 2 and the cross section is circular.

The silicone rubber hollow fiber 1 may be, in the range of not exceeding 400 microns in diameter and not exceeding 50 microns in wall thickness, of the same internal and external diameters, or a plurality of kinds thereof having the same internal diameter but having each external diameter different from each other may be used.

The bundling density of the hollow fiber may be either uniform or ununiform. The volume ratio, that is, the volume occupied by the hollow fibers within the housing, may be preferably 10 to 70%.

As shown, FIG. 1 shows the housing being formed as a cylinder in section with the end thereof being closed, wherein a first inlet A and a first outlet B are formed on both end walls of housing $H_1$, respectively. A second inlet C and outlet D are formed on the side wall of housing $H_1$ with a prescribed distance therebetween in the opposite radial direction to each other. Housing $H_1$ may have also an elliptic section, whereby the module $M_1$ may have an elliptic section.

Hollow fiber module $M_1$ is received within the housing $H_1$, the ends being sealed to housing with silicone resin, and core 2 is closed at both ends also with silicone resin.

As mentioned above, in the enclosed state, the internal and external circulation passages for module $M_1$ are formed within the housing H1. The internal passage being formed inside the hollow fibers is in communication with first inlet and second inlet B, while the external passage formed outside the silicone wall is in communication with the second inlet and passages C and D.

Figure 2:
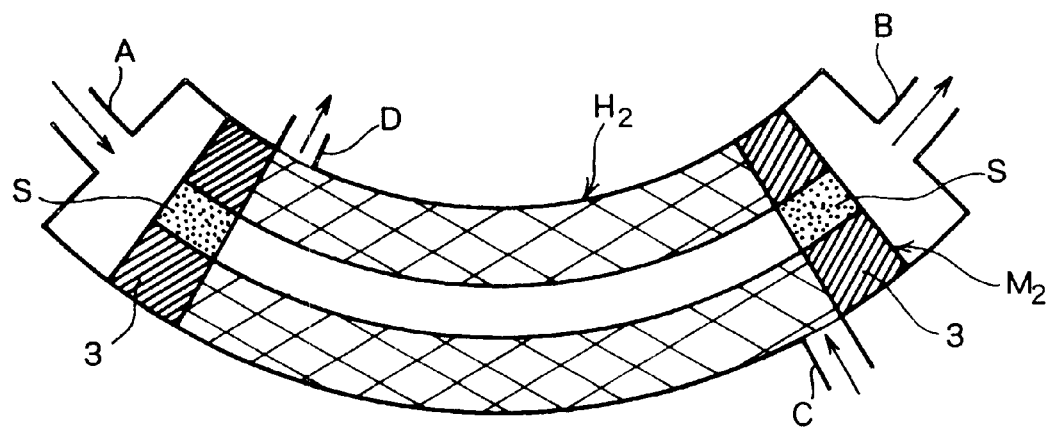
FIG. 2 is a sectional view schematically illustrating a gas exchange apparatus according to another embodiment.
Figure 3:
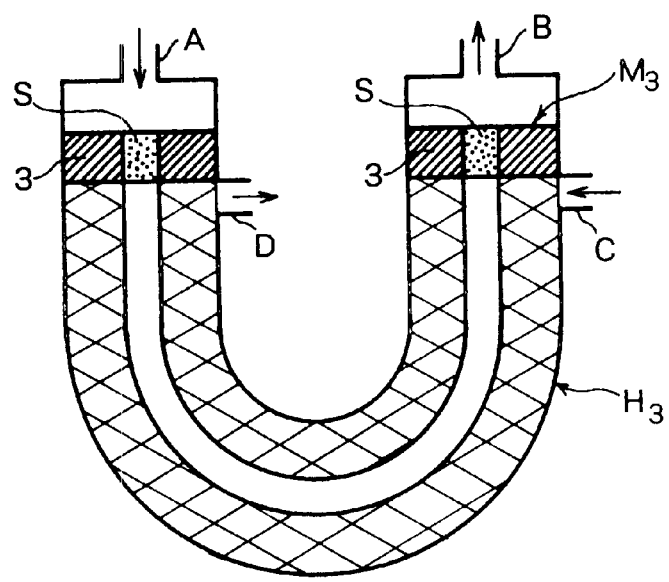
FIG. 3 is a sectional view schematically illustrating a gas exchange apparatus according to a further embodiment.

Gas exchangers shown in FIGS. 2 to 9 are those modified from that shown in FIG. 1. These are also included in the scope of the invention. Those shown in FIGS. 2 and 3 are different from that in FIG. 1 in the shape of the housings $H_2$ and $H_3$, respectively. Namely, these housings are modified in a curved form and a U-shaped form, respectively.

Figure 4:
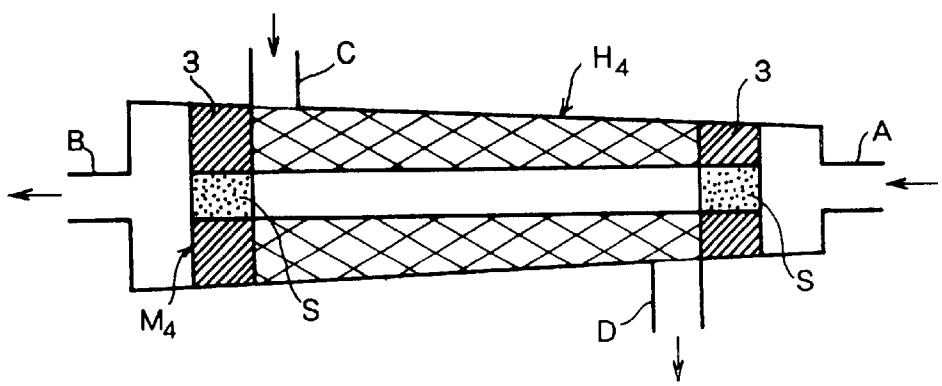
FIGS. 4, 5 and 6 are sectional views schematically illustrating each gas exchange apparatus according to embodiments similar to but modified from those in FIGS. 1, 2 and 3, respectively.
Figure 5:
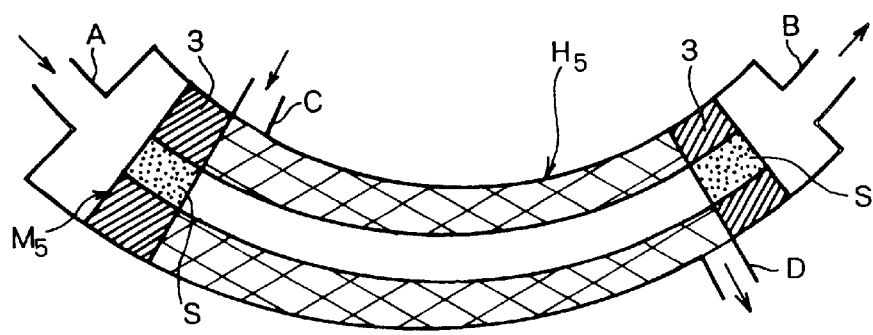
Figure 6:
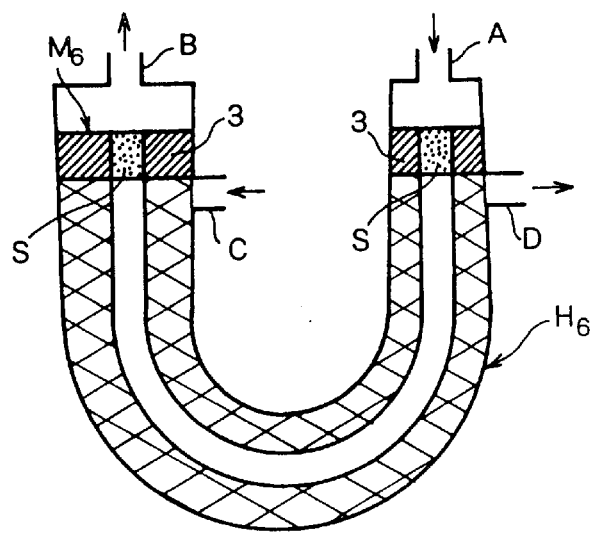

Similarly, housings $H_4$, $H_5$ and $H_6$ in FIGS. 4, 5 and 6 are, respectively, modified from FIGS. 1, 2 and 3 so as to be gradually slimmed from one end toward the other end along the axial direction of the housing.

The hollow fiber modules $M_2$, $M_3$, $M_5$ and $M_6$ are received into the housings $H_2$, $H_3$, $H_5$ and $H_6$, respectively, after removing the cores from each housing. When preparing the modules $M_4$ to $M_6$ in twill wound form, the bundling density of the minor diameter is relatively larger than the major.

Figure 7:
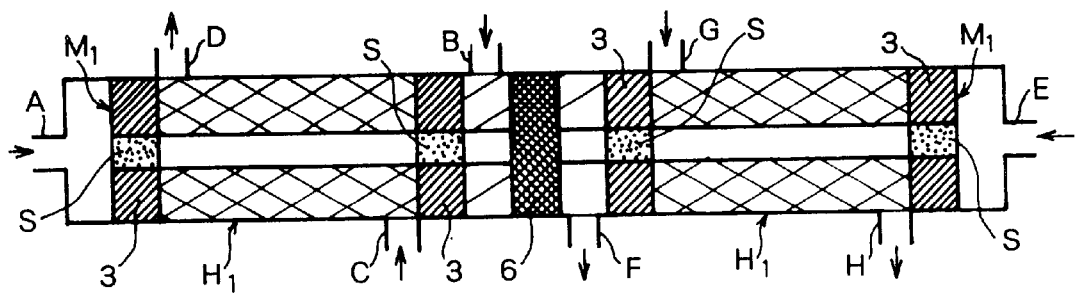
FIGS. 7, 8 and 9 are sectional views schematically illustrating each gas exchange apparatus according to each of further modified embodiments, respectively.

A gas exchanger shown in FIG. 7 is of the form of two exchange units in FIG. 1 combined in series together with a partition 6 interposed therebetween, having the first inlets A and E, first outlets B and F, second inlets C and G, and second outlets D and H.

The use of such a gas exchanger of the type is as follows: with the first inlet E of the one unit being closed, by lowering the pressure through the first outlet F, the venous blood is introduced from the inlet G and exhausted from the outlet H; thus gases $CO_2$, $N_2$ and $O_2$ are extracted from the venous blood. The blood is further introduced to the second inlet C, and added with $N_2$ and $O_2$ which are introduced through first inlet A and further added with a small amount of $CO_2$ to convert the blood to the arterial blood, which is collected from the second outlet D.

Figure 8:
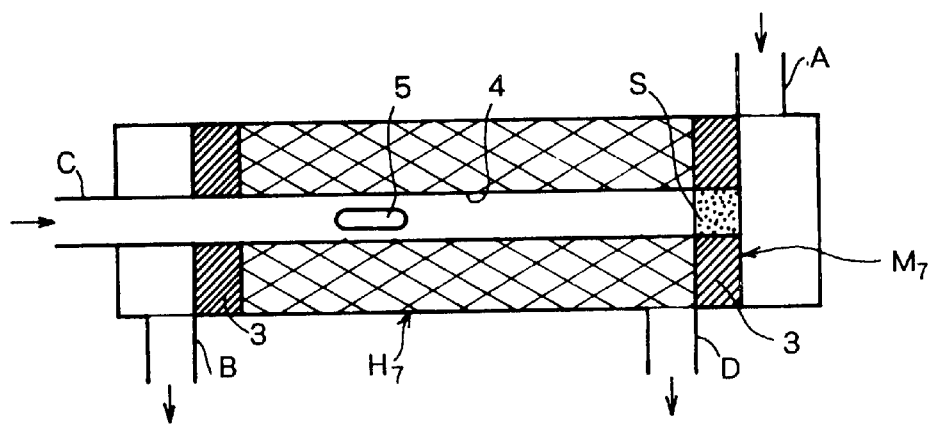

A gas exchanger shown in FIG. 8 is provided with a core 4 of the hollow fiber module $M_7$, the core 4 being extended out of the housing $M_7$ to form a second outlet D in communication with the external perfusion passage; from such second outlet D and through an opening 5 formed in the core 4, a liquid or gas is vented to an external perfusion passage and vented from the second outlet D.

Figure 9:
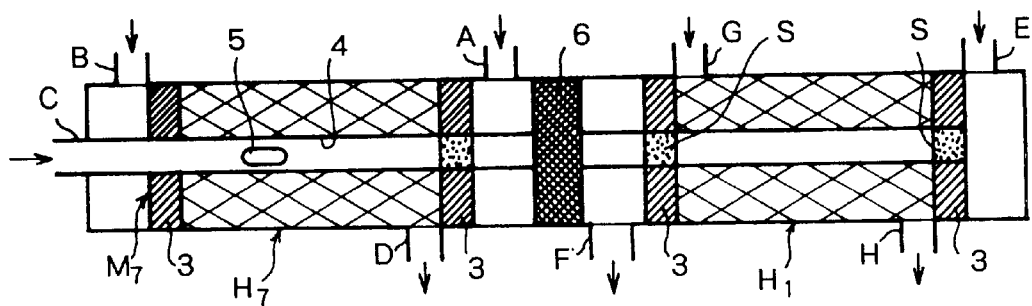
Figure 10:
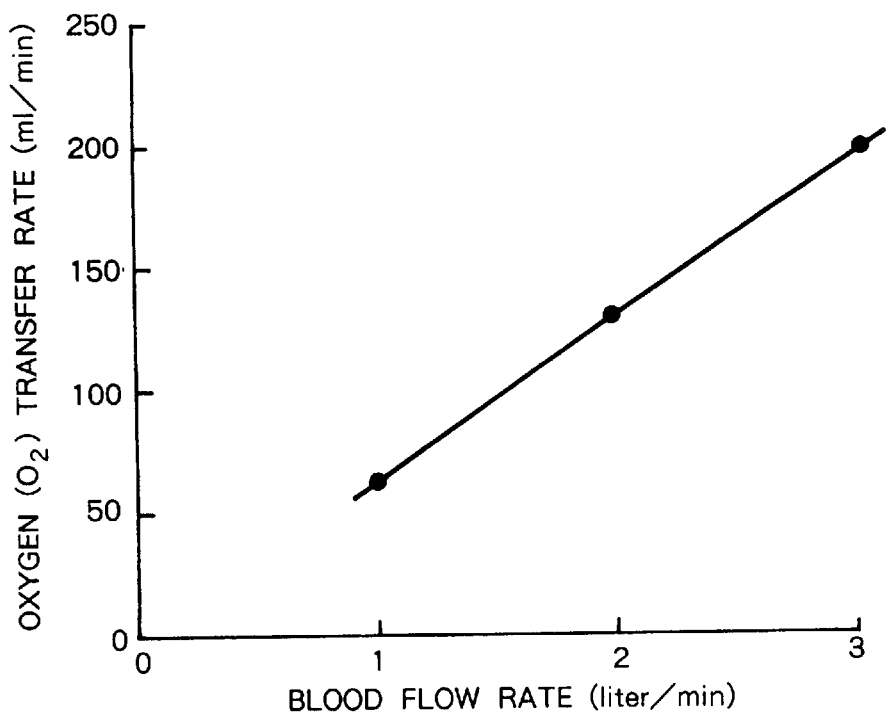
FIG. 10 is a diagram illustrating the gas exchange ability according to the invention.
Figure 11:
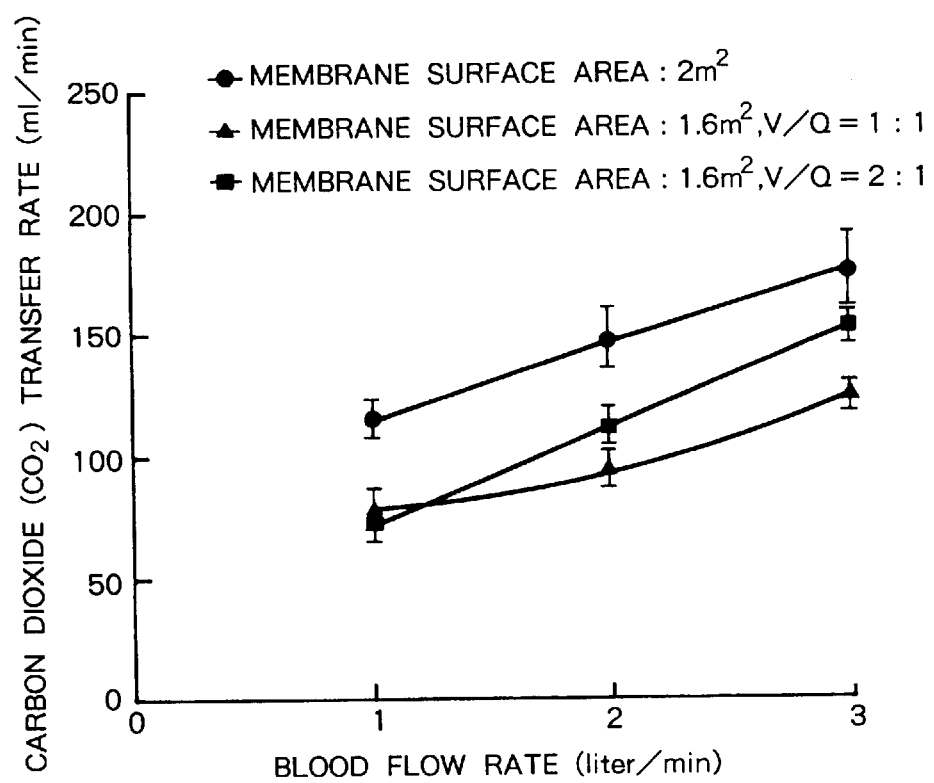
FIG. 11 is another diagram illustrating the gas exchange ability according to the invention.

The gas exchanger in FIG. 9 is formed so that the left unit of the apparatus shown in FIG. 7 is replaced by the gas exchanger of FIG. 8.

The fundamental structures in FIGS. 2 to 9 other than described above are not essentially different from that in FIG. 1.

According to the invention, any elongation or excessive wound stress or the like of the hollow fiber is prevented even a considerable tension is applied, because of using a silicone rubber fiber having a thin wall thickness but having sufficient toughness.

Therefore, the hollow fiber may be formed by an arbitrary density, thereby the volume ration of the silicone rubber hollow fiber relative to the internal volume of the housing being enabled to be arbitrarily set. At this time, by using the different size of hollow fibers, the same effect can be achieved as changing the bundling density.

According to the invention, the filling density of silicone rubber fibers in the hollow fiber module, the crossing angle of the hollow fibers, as well as the volume ratio between the occupied area of fibers and internal volume of housing (the hollow fiber filling density), may be also arbitrarily selected.

Accordingly, the flow of liquid within the internal and external perfusion passages, more particularly the disturbance flow of the gas or liquid are adequately controlled, thereby the gas exchange rate being increased to allow the apparatus to be small-sized and the priming volume to be reduced.

Hereinafter described are the preparation of the artificial lung and an in vitro evaluation thereof. The gas exchanger shown in FIG. 1 as an artificial lung has been prepared through the following procedures:

A. Preparation of an Artificial Lung:

Using the composition comprising the components (a) to (e), each of silicone rubber hollow fiber, having an external diameter of 400 microns, wall thickness of 50 microns, and tensile loading ($M_{100}$) of 5 grams, was prepared. A number of hollow fibers above were twill wound and bundles to form the modules $M_1$ of the types I and II, each of which was enclosed within each housing $H_1$ of types I and II to form an internal perfusion passage in each housing Hi for communication with first inlet A and outlet B, and for communication with second external inlet and C outlet D, respectively.

A Hollow Fiber Module of Type I:

4000 pieces of silicone rubber hollow fibers 1 were uniformly twill bundled around a core of 120° to form cylindrical module having an external diameter of 50 mm, a length of 200 mm and a length of each sealed end 3 being 5 mm.

A Hollow Fiber Module of Type II:

A cylindrical module having an external diameter of 57 mm, a length of 200 mm and a length of each sealed end 3 being 8 mm: formed of 4600 pieces of silicone rubber hollow fibers uniformly twill bundled around a core having an external diameter of 8 mm, with a crossing angle of 120°.

A Housing of Type I:

An end-closed housing formed of polycarbonate in a cylinder having an internal diameter of 48 mm and a length of 200 mm, provided with a first inlet, a first outlet B, a second inlet C and a second outlet D.

A Housing of Type II:

A cylindrically formed housing having both ends thereof closed, formed of polycarbonate, having an internal diameter of 55 mm, and a length of 200 mm, provided with a first inlet A, a first outlet B, a second inlet C, and a second outlet D.

Each of modules $M_1$ of types I and II above includes silicone rubber hollow fibers 1, wherein the fibers were sealed at both ends with silicone resin, thereafter the sealed portions were cut away along the radial direction.

The volume ratio of silicone rubber hollow fibers relative to the sectional area of the housing $H_1$ was 35%. The effective membrane area of the housing $H_1$ was 1.6 m² in the case using the type I, and 2 m² in the case of type II.

The breakdown strength of the rubber of silicone hollow fiber 1 was from about 950 to 2100 g/mm², which was twice that of the conventional silicone rubber hollow fiber.

The internal and external perfusion passages were formed by sealing the housing $H_1$ with the second portion 3 of module $M_1$ with silicone resin, and closing the both ends with also silicone resin.

In the closed state of module $M_1$ within housing $H_1$ in either case of type I or II, an internal and an external perfusion passages for fiber module $M_1$ are formed in the housing $H_1$. The first inlet A together with the first outlet B provides the entrance/exit for internal perfusion passage, while a second inlet C and a second outlet D provides the entrance/exit for external perfusion passage.

In practice of the embodiment, three pieces of artificial lungs of type I each comprising a hollow fiber module of type I together with a housing of type I, and, three pieces of artificial lungs of type II each comprising a hollow fiber module of type II together with a housing of type II, were prepared, each of which was evaluated in vitro as follows.

B. Evaluation of Artificial Lungs in Vitro:

Evaluation in vitro was performed using fresh cow blood in such a manner that preparing 20 liters of the blood added with ACD-A solution as the anti-coagulant at the collecting time, which was converted to the standard venous blood by a commercially available artificial lung to be subjected to evaluation in vitro. The blood was fed to the external perfusion passage, and oxygen (by gas state) was supplied through the internal perfusion passage.

The blood circuit was formed by a tube having an inner diameter of ⅜ inches connected to second inlet C, and a boat for collecting blood and measuring the pressure was provided adjacent the inlet C and outlet D. The blood circulation was carried out by a roller pump attached to the tube.

The rate of blood flow was 1, 2 or 3 liter/min, oxygen flow in the artificial lung of type I was by the ratio of oxygen flow Q versus blood flow V (V/Q) being 1 and 2, while the ratio was 1 in the case of the lung of type II.

For reference of mechanical strength, water was filled to the blood side and gas side, with applying an additional pressure of 500 mmHg to the blood side, the volume variation at the gas side was obtained based on the overflown value of filled water. At the same time, a pressure was applied on the gas side in order to obtain the volume change of the blood side.

C. Result of Evaluation:

As to oxygen ($O_2$) transfer rate, in either artificial lung of types I and II, the oxygen saturation rate by each flow rate of blood at the side of second outlet D was as high as 99 to 100%. The transfer rate of carbon dioxide using the lung of type I at a flow rate of 3 liter/min was 108 to 112 ml/min (milliliters per minute) at V/Q=1, and 140 to 146 ml/min at V/Q=2. Accordingly, by increasing the gas flow rate, the transfer rate was increased by 30%.

On the other hand, the transfer rate of carbon dioxide was in the range of from 158 to 164 ml/min in the case using the lung of type II at the same blood flow rate.

The pressure loss was increased in proportion with the blood flow rate in either of the lungs of types I and II, the value of which being 196.64 mmHg at a blood flow rate of 3 liter/min.

The blood filling volume (priming volume) was 150 ml(milli liter) by the lung of type I, and 240 ml by the lung of type II. The change of the blood filling volume caused by additional pressure was measured: as a result, the volume change rate was, at either of the gas side and blood side, in the order of 0.2 to 0.3 ml, which corresponds to 0.1% or so of the blood filling rate.

In the anti-pressure test preliminarily performed, any explosion of the wall was not observed in the pressure range up to 5 kg/cm², corresponding to about 3,760 mmHg, which was applied on the gas side of the artificial lung.

In the evaluation on lungs of types I and II as to gas exchange ability, excellent performance was exhibited so that no difference was observed compared with the commercially available artificial lungs of porous polypropyrene rubber hollow fiber. Also, compared with the conventional lungs formed of silicone hollow fibers having a membrane area of 5 to 7 m², the gas exchange ability of the increased order was confirmed even with the wall area of about ⅓ compared with the conventional.

D. Conclusion:

From the result of in-vitro evaluation above, the following conclusion was obtained:

(1) It has been confirmed that the artificial lung using silicone walled hollow fibers has the gas exchange ability in the same order of that using polypropyrene porous hollow fibers, and has a sufficient performance as an artificial lung.

(2) The silicone walled hollow fiber 1 of the invention has the dimension of about ½ that of the conventional silicone rubber hollow fiber. Therefore, according to the invention, compared with the conventional lung using the conventional silicone rubber hollow fibers, it has been possible to obtain a membrane area of nearly twice that of the conventional lung within the housing having the same volume.

Accordingly, it has been enabled to increase the gas exchange rate per unit volume and also to minimize the priming volume by either of artificial lungs of type I and type II, and thereby the apparatus has been small-sized.

As discussed above, the invention provides a small-sized gas exchange apparatus of high performance having an increased gas exchange rate and a minimized priming volume.

Silicone Rubber Hollow Fiber

The silicone rubber hollow fiber for use in a gas exchange apparatus according to the present invention is produced by making use of a silicone rubber composition proposed by the applicant in a prior application, Japanese Patent Application No. 159899/1996 by the same applicant, and further improved as hereinafter described in detail.

Therefore, the present invention also relates to a silicone rubber hollow fiber having an outer diameter of less than 400 microns and a wall thickness of less than 50 microns formed of a silicone rubber composition comprising:

(a) 100 parts by weight of organopolysiloxane having a viscosity in the range of 10,000 to 10,000,000 poise at 25° C. containing at least two alkenyl groups, (b) 5 to 50 parts by weight of organosiloxane copolymer which is constituted by triorganosiloxane unit illustrated by the following general formula;

(wherein R is substituted or non-substituted monovalent hydrocarbon group having 1 to 10 carbon atoms) and SiO2 unit, the mole ratio of said triorganosiloxy unit to said SiO2 unit of which is 0.5 to 1.2)

(c) sufficient amount of organohydrogensiloxane having at least two hydrogen atoms directly bonded to silicon atom in a molecule to supply 0.5 to 10 mole of hydrogen atoms directly bonded to silicon atom to vinyl groups of components (a) and (b), (d) catalytic amount of platinum or platinum compounds, and (e) 10 to 150 parts by weight of fine powdered silica having a specific surface of more than 50 m²/g.

The process for producing the silicone rubber hollow fiber provided by this invention is a process for producing a silicone rubber hollow fiber by making use of the silicone rubber composition aforesaid and is characterized in that when said silicone rubber composition is extruded from a nip between a die and a nipple of an extruder and oriented under heating in a vulcanizer, an oriented sectional area $S_1:S_2$ is set in the range from 1:0.5 to 1:0.01 wherein $S_1$ is a sectional area of a tube extruded from the nip between the die and the nipple of the extruder and $S_2$ is a sectional area of a tube oriented.

The silicone rubber composition used in this invention is not particularly limited and may be ones which can be extruded in the form of tube. And the method for curing may be an addition curing or organicperoxide curring-type, but an addition curing-type silicone rubber composition may be preferably and above all the silicone rubber composition comprising (a)alkenyl group-containing organopolysiloxane, (b)organopolysiloxane copolymer, (c)organohydrogensiloxane, (d) platinum compound and finely powdered silica may be most preferable.

The aforesaid silicone rubber composition is explained in more detail.

The organopolysiloxane of component(a)is one having a viscosity in the range of 10,000 to 10,000,000 poise at 25° C., preferably 80,000 to 1,000,000 poise.

The organopolysiloxane of component (a) is one having at least 0.001–1 percent by weight, preferably 0.002–0.2 percent by weight of at least two vinyl groups, allyl group or alkenyl group having 2–8 carbon atoms such as propenyl group, preferably vinyl group. And an organic group except for the alkenyl group is non-substituted or substituted monovalent hydrocarbon group having 1–8 carbon atoms and having no aliphatic nonsaturated group. As the organopolysiloxane may be preferably one illustrated by the following general formula:

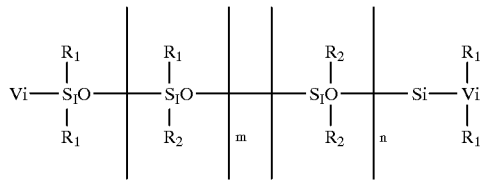

(Wherein Vi is a vinyl group, $R_1$, is a non-substituted or substituted monovalent hydrocarbon group having 1–10 carbon atoms such as alkyl group, alkenyl group, aryl group, aralkyl group and most preferably selected from the group consisting of vinyl group, phenyl group, alkyl group having 1–8 carbon atoms, fluoroalkyl group having 3–10 carbon atoms and mixture thereof. $R_2$ is a non-substituted or substituted monovalent hydrocarbon group having 1–10 carbon atoms and having no aliphatic unsuturated group and may be preferably selected from the group consisting of phenyl group, alkyl group having 1–8 carbon atoms, fluoroalkyl group having 3–10 carbon atoms and mixture thereof. m and n are numbers which are selected so that the viscosity of the component (a) is in the range from 10,000 to 10,000,000 poise at 25° C. and the concentration of vinyl group is in the range from 0.01 to 1 percent by weight.)

The alkyl group shown by $R_1$ and $R_2$ are exemplified by methyl group, ethyl group, propyl group and the fluoroalkyl group may be exemplified by 3,3,3-trifluoropropyl group. And R may be preferably vinyl group or methyl group, $R_2$ may be methyl group.

The organopolysiloxane of component (b) has an effect for imparting a viscosity to the silicone rubber before curing and for improving the formability of hollow fiber. The component (b) is anorganopolysiloxane copolymer of a triorganosiloxane unit illustrated by the following general fromula:

(Wherein R may be non-substituted or substiuted monovalent hydrocarbon group having 1–10 carbon atoms such as alkyl group, alkenyl group, aryl group, halogenated alkyl group and may be preferably selected from the group consisting of vinyl group, phenyl group, alkyl group having 1–8 carbon atoms, fluoroalkyl group having 3–10 carbom atoms and mixture thereof.) and $S_1O_2$ unit. The alkyl group shown by R may be exemplified by methyl group, ethyl group, propyl group and fluoroalkyl group may be exemplified by 3,3,3-trifluoropropyl group. More preferably,R is vinyl group or methyl group.

The mole ratio (M/Q) of triorganosiloxy unit to $S_1O_2$ unit may be in the range from 0.6 to 1.2. In the case where the triorganosiloxy unit is in large quantity beyond 1.2, the viscosity of the composition before curing is high and the workability is remarkably decreased. On the contrary,in the case that the triorganosiloxy unit is in small quantity beyond 0.6, the viscosity of the organopolysiloxane copolymer becomes too high or the amount of silanol remained is highly increased and the stable synthesis can be hardly carried out. The mole ratio (M/Q) of triorganosiloxy unit to $S_1O_2$ unit may be preferably in the range from 0.7 to 1.1.

The organopolysiloxane copolymer of the component (b) may contain the other units except for $S_1O_2$ unit and triorganosiloxy unit, for example $RS_1O_{3/2}$, $R_2S_1O_{2/2}$ (R is the same as aforedefined). The organopolysiloxane copolymer of this kind may be produced by the publicly known process; For example, it can be easily synthesized by mixing $R_3S_1Cl$ with $S_1Cl_4$ to effect co-hydrolytic condensation.

The component (b) may be compounded in 5–50 parts by weight to 100 parts by weight of the component (a). When it is less than 5 parts by weight, the improvements in modulus and tear strength are poor, and the stabilization of orientation ratio at the time of forming hollow fiber becomes difficult and also the wall thickness of the hollow fiber formed is not uniform. On the contrary, when it is more than 50 parts by weight, an elongation of rubber cured is decreased and the viscosity of the rubber compound before curing is increased to result in poor workability. And accordingly, the range from 7–40 parts by weight may be preferably.

The organohydrogensiloxane of component (c) acts as a crosslinking agent on alkenyl group-containing organopolysiloxane of components (a) and (b) and contains indispensably at least two hydrogen atoms bonded directly to silicon atom ($\equiv S_1H$ bond).

When the organohydrogenslioxane is below in the amount to supply 0.5 mole of $\equiv S_1H$ groups to alkenyl group of sum of the components (a) and (b), the hydroxylation reaction becomes insufficient. When the organohydrogensiloxane is beyond the amount to supply 10 mole of $S_1H$ groups, the products becomes brittle and surplus $\equiv S_1H$ bonds remain to result in an aging. It is, therefore, required that the amount of organohydrogensiloxane is in the range to supply 0.5–10 mole of hydrogen atoms bonded directly to silicon atom to alkenyl groups of sum of the components (a) and (b) and may be preferably in the range from 1 to 7 moles.

The organohydrogensiloxane of this kind may be straight-chain, branched-chain and cyclic providing it contains at least two hydrogen atoms bonded directly to silicon atom in a molecule and may be preferably one illustrated by the following general formula;

$Ra^3H_bSiO(4-a-b)/2$ (Wherein $R_3$ has the same meaning as $R_2$ aforedefined and may be preferably methyl group. a and b are the numbers sufficient for satisfying inequalities $0 \leq a < 3$, $0 < b \leq 2$ and $0 < a+b < 4$. The organohydrogensiloxane of this kind may be exemplified by dimethylhydrogensilyl-terminal hindered straight organopolysiloxane, organopolysiloxane having dimethylsiloxane unit and dimethylhydrogensiloxane unit in main chain terminals of which are hindered by trimethylsilyl group, low viscous fluid having dimethylhydrogensiloxane unit and $SiO_2$ unit, 1,3,5,7-tetrahydrogen-1,3,5,7-tetramethyl cyclotetrasiloxane, 1-propyl-3,5,7-trihydrogen-1,3,5,7-tetramethylcyclotetrasiloxane and 1,5-dihydrogen 3-.7-dihexyl,3,5,7-tetramethylcyclotetrasiloxane.

The platinum or platinum compound of component (d) is an addition reaction catalyst publicly known to the art and may be platinum black or platinum carried on silica or carbon black, chloroplatinic acid or alcohol solution of chloroplatinic acid, complex salt of chloroplatinic acid with olefin or vinylsiloxane. The addition amount of the component (d) may be preferably in the range from 0.0001 to 0.1 parts by weight to 100 parts by weight of each components of (a), (b) and (c) to achieve the practical curing ratio. The silica of component (e) may be preferably silica having a specific surface area of more than 50 m²/g, preferably in the range from 100 to 400 m²/g in order to improve the mechanical strength such as hardness and tensile strength. As the silica of this kind may be used fumed silica, precipitated silica or mixture thereof. Above all may be preferably fumed silica-hydrophbic treated with chlorosilane or silazane. In this case, the hydrophbic fumed silica containing carbon in the range from 0.8 to 5.0, preferably in the range from 1.0 to 3.0 percent by weight to total weights of fillers can contribute effectively the improvement in modulus and tensile strength and increase the strength and elasticity of the cured silicone rubber film and prohibited the film from bursting, which results in an increase in the orientation ratio at the time of orientation treatment step. From this point of view, the hydrophobic fumed silica may be preferably used. The hydrophobic fumed silica of this kind may be available from the market and exemplified by AEROSIL R-976, AEROSIL R-974(NIHON AERISIL Co., Ltd), AEROSIL R-812D (DEGUSSA), RHEOLOSIL DM-30S, RHEOLOSIL DM-20S(TOKUYAMA Co., Ltd).

The silica of component (e) may be added in the range from 10 to 150 parts by weight, preferably 20 to 100 parts by weight to 100 parts by weight of organosiloxane of component (a). When the amount of silica to be added is beyond the range, the complex coefficient of viscosity of the silicone rubber composition at a temperature of 25° C. is beyond the range from $1 \times 10^4$ Pa·s to $1 \times 10^8$ Pa·s at 0.01Hz and, as a result, a sufficient mechanical strength of hollow fiber oriented can not be obtained.

To the silicone rubber composition may be added, if necessary, conventional fillers in the range not to disturbed the object of this invention. Such the fillers are, for example, powdered silica, diatomaceous earth, iron oxide, titanium oxide, carbon black, barium oxide, magnesium oxide, cerium oxide, calcium carbonate, magnesium carbonate, zinc carbonate, molten silica powder. Acetylene alcohols for controlling the curing reaction ratio, that is pot-life, hydroperoxides, organic peroxides for accelerating vulacanization-curing, silanole-contaiing low-molecular siloxanes or alkoxysilanes as dispersing agent, pigments, dyes, antioxidants, chemical destaticizers may be added to the silicone rubber composition.

As described above, the silicone rubber composition used by this invention has the following three characteristics;

(1) Since the organopolysiloxane copolymer is compounded to the silicone rubber composition, the hollow fiber formed therefrom has a tensile loading (M 100) of more than 5 g and sufficient retentivity of shape for thin-gage of film thickness.

(2) Since the surface of the fine powdered silica, a main component of the silicone ruber composition is hydrophobic-treted with chlorosilane or silazane, the silica in the silicone rubber is not agglomerarted and dispersed uniformly. And accordingly, the silicone rubber composition is not cut during the step of extruding in the form of tube and orientation.

(3) The silicone rubber composition is superior in orientation poformance for its low viscosity coefficient.

(4) Since the silicone rubber composition has the characteristics described in (1)–(3) above mentioned, even a hollow fiber having an outer diameter of less than 400 μm and a wall thickness of less than 50 μm can be easily produced.

EXAMPLE

While this invention is explained with reference to examples together with comparative examples, it should be understood that this invention is not limited to the specific examples given but can be modified in various ways without from the spirit of this invention.

Examples 1–7

The components were used in amount of parts by weight shown in Table 1 and kneaded in a mixing roll.

Raw rubber-1, raw rubber-2, resin-1, resin-2, platinum catalyst, cross-linking agent, filler-1, filler-2 and dispersing agent shown in Table 1 are explained below;

(1) Raw Rubber-1

An organopolysiloxane raw rubber consisiting of dimethylsiloxy unit, methylvinylsiloxy unit and dimethylvinylsiloxy unit, having a viscosity of 300,000 poise at 25° C. and vinyl contents of which are 0.054 wt %.

(2) Raw Rubber-2

An organopolysiloxane raw rubber consisiting of dimethylsiloxy unit, methylvinylsiloxy unit and dimethylvinylsiloxy unit, having a viscosity of 300,000 poise at 25° C. and vinyl contents of 0.019 wt %.

(3) Resin-1

An organopolysiloxane copolymer consisiting of $SiO_2$ unit, dimethylvinylsiloxy unit and trimethylsiloxy unit wherein the mole ratio of dimethylvinylsiloxy unit and trimethylsiloxy unit to $SiO_2$ is 1:0.12:0.94, having vinyl contents of 2 wt % and a viscosity of 50% toluene solution of 3.5 cs at 25° C.

(4) Resin-2

An organopolysiloxane copolymer consisiting of $SiO_2$ unit, dimethylvinylsiloxy unit and trimethylsiloxy unit wherein the mole ratio of dimethylvinylsiloxy unit and trimethylsiloxy unit to $SiO_2$ is 1:0.06:0.9, having vinyl contents of 2.3 wt % and a viscosity of 50% toluene solution of 5 cs at 25° C.

(5) Platinum Catalyst

A platinum catalyst of octyl alcohol solution of chloroplatinic acid the platinum content in which is 1 wt %.

(6) Cross-linking Agent

A methylhydrogenpolysiloxane containing 17 mole % of methylhydrogen-polysiloxane units terminals of which are hindered by dimethylhydrogen-siloxy groups, having a viscosity of 12 cs.

(7) Filler-1

A silica AEROSIL R-812 available from DEGUSSA, having a specific surface of 260 $m^2/g$ and carbon contents of 2.5 wt %.

(8) Filler-2

A silica AEROSIL 300 available from NIHON AEROSIL Co., Ltd. having a specific surface of 300 $m^2/g$.

(9) Dispersing agent

A dimethylpolysiloxane having silanol groups at both terminals, having a viscosity of 20 cs at 25° C.

The silicone rubber composition obtained was extruded in the form of tube from an extruder equipped with a cylinder a diameter of which is 40 mm, a die and a nipple in which the ratio of the length of cylinder (L) to diameter thereof (D), (L/D) is 12. The tube thus extruded was oriented under heating by passing through a heating oven maintained at 25–500° C. at a rate of 200–10,000 m/hr. The hollow fiber cured at the first curing step by passing through the heating oven was subjected to postcuring in a dryer at 180° C. for two hours. The sizes of the die and nipple used are listed in Table 2.

For comparison, the components for comparative examples shown in Table 2 were kneaded and oriented and subjected to postcuring according to the same procedures as examples. The evaluations of the hollow fiber obtained were as follows;

(1) While the silicone rubber compositions of comparative examples 1–3 were extrudable, an orientation could not be stably carried out because of being cut. Checking the portion which was cut, it was found that the silicone rubber tube of the portion was elongated to become fine and a uniform orientation was not achieved.

(2) The silicone rubber compositions of examples 1–7 were extrudable. The tensile loading ($M_{100}$) was 5 g and over.

(3) While the tubes of silicone rubber compositions of examples 6 and 7 were elongated to become fine and include portions sizes of an outer diameter and wall thickness of which were not uniform, the sizes of the outer diameter and wall thicknes were in the range of ±10 μm.

(4) The tubes of silicone rubber compositions of examples 2–5 were stable at their sizes of outer diameter and wall thickness and could be oriented uniformly and produced continuously.

It can be seen from the results as above explained that when the silicone rubber compositions of examples were extruded in the form of tube and subsequently were cured in a vulcanizer, while in the case where the ratio of oriented sectional area $S_1$: $S_2$ is 1:0.01 or less, the continuous production of tube is not possible because of being cut during the continuous extrusion, in the case where the $S_1$: $S_2$ is 1:0.5 or more, the sizes of outer diameter and wall thickness are not stable and the tube itself is elongated of its own weight or the tube having expected sizes can not be obtained.

As above explained, according to the process for producing a hollow fiber of silicone rubber composition of this invention, a fine and thin-gage silicone rubber hollow fiber having a tensile loading ($M_{100}$) of more than 5 g and an outer diameter of less than 400 μm.

And also, since the hollow fiber of this invention is high in a tensile loading ($M_{100}$) and fine with thin-gage wall, a gas permeability rate can be increased and a minimization of apparatus is made possible. And a development of an artificial lung of long-term usable with neither leak of blood plasma nor damage to red blood corpuscle and blood platelet is made possible. And a deaerator, gas exchanger, incubator, chemical compounds-removing apparatus which are making use of silicone rubber tube of high-performance and undersize as well as weight-saving can be made possible.

TABLE 1

| Components | Embodiments (Number) | | | | | | | Comparative Examples (Unit: Parts by weight) | | |
|---|---|---|---|---|---|---|---|---|---|---|
| | 1 | 2 | 3 | 4 | 5 | 6 | 7 | 1 | 2 | 3 |
| Law rubber - 1 | 100 | 40 | 20 | 100 | | 80 | 100 | 100 | 80 | 100 |
| Law rubber - 2 | | 60 | 80 | | 100 | 20 | | | 20 | |
| Resin - 1 | 7 | 15 | | | 15 | | | 7 | | 7 |
| Resin - 2 | | | 15 | 15 | | | | | | |
| Filler - 1 | 65 | 70 | 75 | 75 | 75 | 70 | | 100 | | |
| Filler - 2 | | | | | | | 85 | | 80 | 150 |
| Dispersing agent | 1 | | 1 | 1 | | 20 | 8 | 1 | 20 | 1 |

TABLE 2

| | | EMBODIMENTS | | | | | | Compar. Examples (Unit: Parts by weight) | | |
|---|---|---|---|---|---|---|---|---|---|---|
| | | 1 | 2 | 3 | 4 | 5 | 6 | 7 | 1 | 2 | 3 |
| Internal diameter of die | (r2 mm) | 0.4 | 0.5 | 0.9 | 1.3 | 2.0 | 2.7 | 2.7 | 0.9 | 2.0 | 2.7 |
| External diameter of nipple | (r2 mm) | 0.3 | 0.3 | 0.5 | 1.0 | 1.5 | 1.7 | 2.0 | 0.5 | 1.5 | 2.0 |
| External diameter of hollow fiber | (r3 microns) | 250 | 145 | 190 | 305 | 300 | 270 | 400 | 140 | 180 | 200 |
| Internal diameter of hollow fiber | (r4 microns) | 160 | 90 | 105 | 230 | 210 | 170 | 300 | 80 | 135 | 150 |
| Stretch. section rate S2/S1 *1 | | 0.5271 | 0.0807 | 0.1678 | 0.0582 | 0.0262 | 0.0100 | 0.2128 | 0.0236 | 0.0081 | 0.0053 |
| Wall thickness (micron) of hollow fiber | | 45 | 27 | 42 | 37 | 45 | 50 | 50 | 30 | 22 | 25 |
| Tensile loading (M100)(g)*2 | | 5 | 7 | 9 | 10 | 16 | 5 | 5 | 5 | | |
| Workability | | ◯ | ◯ | ◯ | ◯ | | | | x | x | x |

*1 S1 = $\pi r1^2 - \pi r2^2$, S2 = $\pi r3^2 - \pi r4^2$
*2 100% modulus (weight at 100% stretching of hollow fiber)

We claim:

1. A gas exchange apparatus for use as an artificial lung comprising:
a hollow fiber module formed by bundling a plurality of silicone rubber hollow fibers wound in the form of a twilled pattern, wherein said hollow fiber having not exceeding 400 microns in external diameter, not exceeding 50 microns in rubber thickness, and 100% elongation load strength of not lower than 5 g, composed of a silicone rubber composition including:
   (a) 100 parts by weight of organo-polysiloxane having a viscosity in the range of 10,000 to 10,000,000 poise;
   (b) 5 to 50 parts by weight of organo-polysiloxane copolymer essentially formed of:
      a triorganosiloxy monomer represented by the following formula: $R_3SiO_{1/2}$, where R is a non-substituted or substituted monovalent hydrocarbon group having 1 to 10 carbon atoms, and
      a $SiO_2$ unit;
   and having a molar ratio of said triorganosiloxy monomer relative to said $SiO_2$ unit being in the range of from 0.6 to 1.2;
   (c) organo-hydrogen siloxane containing at least two hydrogen atoms each being directly coupled with silicon atom, the amount of said siloxane corresponding to that of supplying hydrogen atoms directly coupled with silicon atom being 0.5 to 10 times by mole relative to vinyl groups contained in said components (a) and (b);
   (d) a catalytic quantity of platinum or a platinum compound; and
   (e) 100 to 150 parts by weight of finely powdered silica having a specific surface area of not less than 50 $m^2gj$;
a housing for enclosing said hollow fiber module;
an internal perfusion passage and an external perfusion passage formed within said housing;
a first inlet and a first outlet formed on said housing for gas or liquid for communication with said internal perfusion passage; and
a second inlet and a second outlet formed on said housing for gas or liquid for communication with said external perfusion passage.

2. A gas exchange apparatus according to claim 1, wherein:
the dimension and bundling density of said silicone rubber hollow fibers being either uniform or uniform;
the volume ratio of the internal volume of said housing relative to the volume of said silicone rubber hollow fibers being in the range of 10 to 70;
the crossing angle of said fibers bundled in a twill figure to form said hollow fiber module being in the range of from 30 to 160 degrees; and
said housing being a cylindrical body having both ends closed, and having a shape selected from the group consisting of a straight, curved and bent forms.

* * * * *

UNITED STATES PATENT AND TRADEMARK OFFICE
CERTIFICATE OF CORRECTION

PATENT NO. : 5,964,725
DATED : October 12, 1999
INVENTOR(S) : Sato et al.

It is certified that error appears in the above-identified patent and that said Letters Patent is hereby corrected as shown below:

Title Page, under "Inventors", delete "Hayama-machi" and insert --Kanagawa-Ken--.
Title Page, ABSTRACT, line 1, delete "a artificial" and insert --an artificial--.
Column 2, line 15, delete "tO" and insert --to--.
Column 2, line 17, delete "an" and insert --a--.
Column 2, line 25, after "even" insert --if--.
Column 2, line 41, delete "(100%" and insert --100%--.
Column 3, line 61, delete "H1" and insert --$H_1$--.
Column 3, line 62, after "inlet" insert --A--.
Column 4, line 44, after "even" insert --if--.
Column 5, line 8, delete "Hi" and insert --$H_1$--.
Column 5, line 10, delete "and C" and insert --C and--.
Column 5, line 25, after "first inlet" insert --A--.
Column 6, line 32, delete "(milli liter) and insert --(milliliter)--.
Column 7, line 25, delete "$R_3S_1O_{1/2}$" and insert -- $R_3SiO_{1/2}$--.
Column 7, line 28, delete "SiO2" and insert --$SiO_2$--.
Column 7, line 29, delete "SiO2" and insert --$SiO_2$--.
Column 7, line 53, delete "curring-type" and insert --curing-type--.
Column 8, line 10, change all occurrences of "$R_1$" to --$R^1$--.
Column 8, line 10, change all occurrences of "$R_2$" to --$R^2$--.
Column 8, line 15, delete "$R_1$" and insert --$R^1$--.
Column 8, line 24, delete "unsuturated" and insert --unsaturated--.
Column 8, line 32, delete "$R_1$ and $R_2$" and insert --$R^1$ and $R^2$--.
Column 8, line 35, delete "R" and insert --$R^1$--.
Column 8, line 41, delete "fromula" and insert --formula--.
Column 8, line 51, delete "$S_1O_2$" and insert --$SiO_2$--.
Column 8, line 56, delete "$S_1O_2$" and insert --$SiO_2$--.
Column 8, line 65, delete "$S_1O_2$" and insert --$SiO_2$--.
Column 8, line 67, delete "$S_1O_2$" and insert --$SiO_2$--.
Column 9, line 1, delete "$RS_1O_{3/2}$" and insert --$RSiO_{3/2}$--.
Column 9, line 1, delete "$R_2S_1O_{2.2}$" and insert -- $R_2SiO_{2.2}$--.
Column 9, line 4, delete "For" and insert --for--.

UNITED STATES PATENT AND TRADEMARK OFFICE
CERTIFICATE OF CORRECTION

PATENT NO. : 5,964,725
DATED : October 12, 1999
INVENTOR(S) : Sato et al.

It is certified that error appears in the above-identified patent and that said Letters Patent is hereby corrected as shown below:

Column 9, line 5, delete "$R_3S_1Cl$ with $S_1Cl_4$" and insert -- $R_3SiCl$ with $SiCl_4$ --.
Column 9, line 16, delete "preferably" and insert --preferable--.
Column 9, line 21, delete "$S_iH$" and insert --SiH--.
Column 9, line 22, delete "organohydrogenslioxane" and insert --organohydrogensiloxane--.
Column 9, line 23, delete "$S_iH$" and insert --SiH--.
Column 9, line 26, delete "$S_iH$" and insert --SiH--.
Column 9, line 27, delete "becomes" and insert --become--.
Column 9, line 27, delete "$S_iH$" and insert --SiH--.
Column 9, line 37, delete "$Ra^3H_bSiO(4-a-b)/2$" and insert -- $R^3_aH_bSiO_{(4-a-b)}/2$ --.
Column 9, line 38, delete "$R_3$" and insert -- $R^3$ --.
Column 9, line 38, delete "$R_2$" and insert -- $R^2$ --.
Column 9, line 51, delete "3-.7-dihexyl,3,5,7-tetramethylcyclotetrasiloxane" and insert --3-7-dihexyl,3,5,7-tetramethylcyclotetrasiloxane--.
Column 9, line 66, delete "silica-hydrophbic" and insert --silica-hydrophobic--.
Column 9, line 67, "hydrophbic" and insert --hydrophobic--.
Column 10, line 5, delete "prohibited" and insert --prohibit--.
Column 10, line 22, delete "disturbed" and insert --disturb--.
Column 10, line 30, delete "-contaiing" and insert --containing--.
Column 10, line 38, delete "(M 100)" and insert --($M_{100}$)--.
Column 10, line 42, delete "ruber" and insert --rubber--.
Column 10, line 43, delete "hydrophobic-treted" and insert --hydrophobic-treated--.
Column 10, line 44, delete "agglomerarted" and insert --agglomerated--.
Column 10, line 49, delete "poformance" and insert --performance--.
Column 10, line 60, after "without" insert --departing--.
Column 11, line 2, delete "consisiting" and insert --consisting--.
Column 11, line 7, delete "consisiting" and insert --consisting--.
Column 11, line 12, delete "consisiting" and insert --consisting--.
Column 11, line 17, delete "consisiting" and insert --consisting--.
Column 12, line 20, delete "thicknes" and insert --thickness--.
Column 12, Table 1, delete all occurrences of "Law Rubber" and insert --Raw Rubber--.
Column 13, Table 2, "Internal diameter of die", Embodiment 1, delete "(r2 mm)" and insert --(r1 mm).

UNITED STATES PATENT AND TRADEMARK OFFICE
CERTIFICATE OF CORRECTION

PATENT NO. : 5,964,725
DATED : October 12, 1999
INVENTOR(S) : Sato et al.

It is certified that error appears in the above-identified patent and that said Letters Patent is hereby corrected as shown below:

Column 13, Table 2, "Tensile loading", Embodiment 2, delete "7" and insert --5--.
Column 13, Table 2, "Tensile loading", Embodiment 3, delete "9" and insert --5--.
Column 13, Table 2, "Tensile loading", Embodiment 4, delete "10" and insert --7--.
Column 13, Table 2, "Tensile loading", Embodiment 5, delete "16" and insert --9--.
Column 13, Table 2, "Tensile loading", Embodiment 6, delete "5" and insert --10--.
Column 13, Table 2, "Tensile loading", Embodiment 7, delete "5" and insert --16--.
Column 13, Table 2, "Tensile loading", Compar. Examples 2, insert --5--.
Column 13, Table 2, "Tensile loading", Compar. Examples 3, insert --5--.
Column 13, Table 2, delete "(M100)(g)*2" and insert --$(M_{100})(g)*2$--
Column 13, Table 2, "Workability", Embodiment 1, delete "O".
Column 13, Table 2, "Workability", Embodiment 5, insert "O".
Column 13, Table 2, delete "*1 S1=πr1² - πr2², S2= πr 3² - πr4²"
   and insert --*1 $S_1 = -\pi r_1^2 - \pi r_2^2$, $S_2 = \pi r_3^2 - \pi r_4^2$--.
Column 13, line 40, delete "organo-polysiloxane" and insert --organopolysiloxane--.
Column 13, line 43, delete "organo-polysiloxane" and insert --organopolysiloxane--.

Column 14, line 48, delete "uniform or uniform" and insert --uniform or ununiform--.

Column 13, line 53, delete "organo-hydrogen siloxane" and insert
   --organohydrogensiloxane--

Signed and Sealed this

Twelfth Day of December, 2000

Attest:

Q. TODD DICKINSON

*Attesting Officer*                *Director of Patents and Trademarks*